(12) United States Patent
Maeda et al.

(10) Patent No.: US 10,603,683 B2
(45) Date of Patent: Mar. 31, 2020

(54) ULTRASONIC VIBRATOR DRIVING APPARATUS AND MESH NEBULIZER

(71) Applicant: OMRON HEALTHCARE CO., LTD., Muko-shi, Kyoto (JP)

(72) Inventors: Masao Maeda, Kyoto (JP); Hidetaka Togo, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 16/351,569

(22) Filed: Mar. 13, 2019

(65) Prior Publication Data
US 2019/0210055 A1    Jul. 11, 2019

Related U.S. Application Data

(63) Continuation of application No. PCT/JP2017/028912, filed on Aug. 9, 2017.

(30) Foreign Application Priority Data

Sep. 27, 2016 (JP) ................................. 2016-188717

(51) Int. Cl.
H01L 41/09 (2006.01)
B05B 17/06 (2006.01)
B06B 1/06 (2006.01)
B06B 1/02 (2006.01)

(52) U.S. Cl.
CPC ........ B05B 17/0623 (2013.01); B06B 1/0223 (2013.01); B06B 1/06 (2013.01)

(58) Field of Classification Search
CPC ...... B06B 17/0623; B06B 1/0223; B06B 1/06

USPC ..................... 310/316.01, 317–319
See application file for complete search history.

(56) References Cited

FOREIGN PATENT DOCUMENTS

| JP | 57-18208 B2 | 4/1982 |
|----|-------------|--------|
| JP | 9-9652 A | 1/1997 |
| JP | 2003-38646 A | 2/2003 |
| JP | 2014-4211 A | 1/2014 |
| WO | 2005/080793 A1 | 9/2005 |

OTHER PUBLICATIONS

Official Communication issued in International Patent Application No. PCT/JP2017/028912, dated Nov. 14, 2017.

*Primary Examiner* — Thomas M Dougherty
(74) *Attorney, Agent, or Firm* — Keating and Bennett, LLP

(57) ABSTRACT

An ultrasonic vibrator driving apparatus applies a sine-waveform alternating voltage as a drive voltage via a conversion circuit to an ultrasonic vibrator that has a unique resonance frequency. A first current detector that detects a first current that flows from the drive voltage generator to the conversion circuit and a second current detector that detects a second current that flows from the conversion circuit to the ultrasonic vibrator are included. A frequency controller performs control on the drive voltage generator to change the frequency of a square-waveform alternating voltage so that the difference between the first current and the second current is reduced or approaches a minimum.

5 Claims, 8 Drawing Sheets

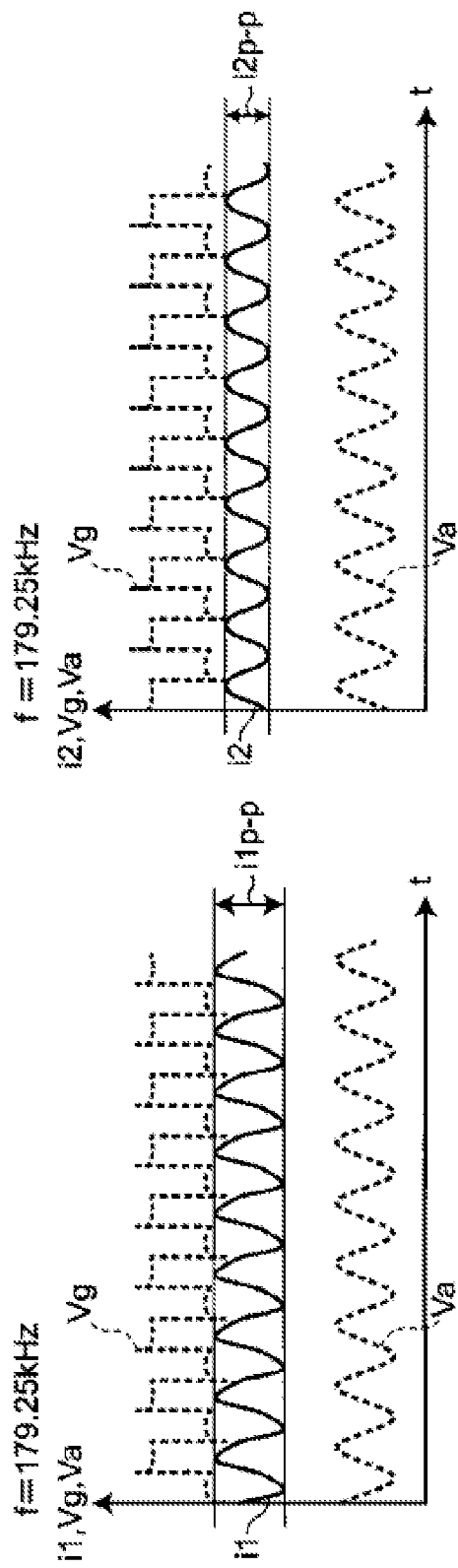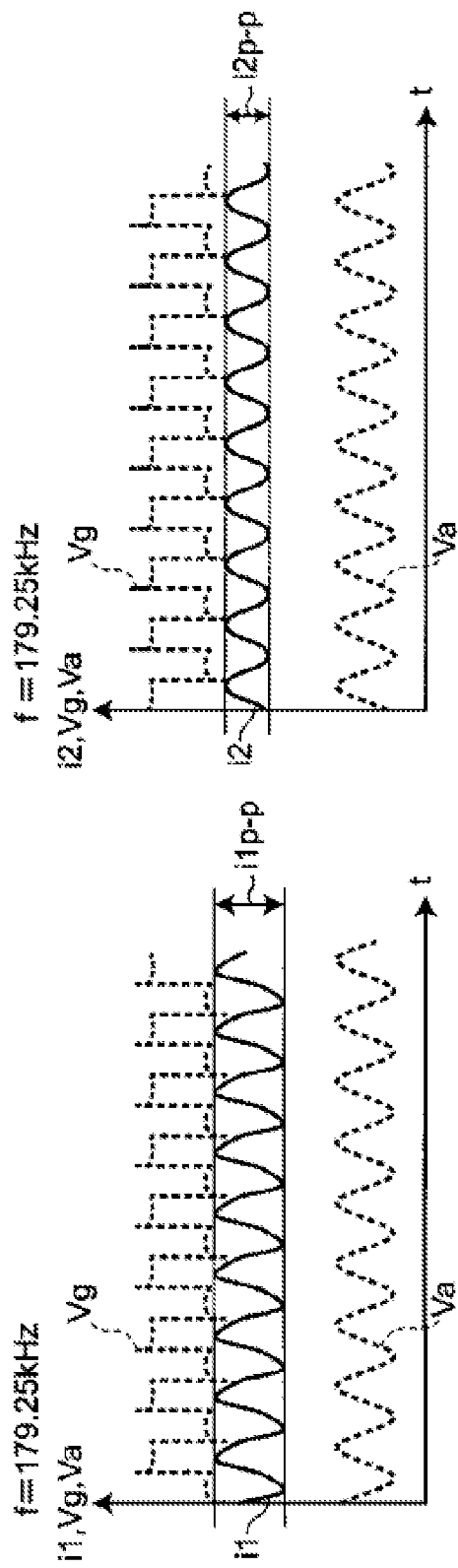

ULTRASONIC VIBRATOR DRIVING APPARATUS AND MESH NEBULIZER

CROSS REFERENCE TO RELATED APPLICATIONS

This application claims the benefit of priority to Japanese Patent Application No. 2016-188717 filed on Sep. 27, 2016 and is a Continuation Application of PCT Application No. PCT/JP2017/028912 filed on Aug. 9, 2017. The entire contents of each application are hereby incorporated herein by reference.

BACKGROUND OF THE INVENTION

1. Field of the Invention

The present invention relates to an ultrasonic vibrator driving apparatus, and more specifically relates to an ultrasonic vibrator driving apparatus that drives an ultrasonic vibrator having a unique resonance frequency by applying a drive voltage (alternating voltage) thereto. Also, the present invention relates to a mesh nebulizer including such an ultrasonic vibrator driving apparatus.

2. Description of the Related Art

Conventionally, for example, JP 2003-038646A has disclosed, as this type of ultrasonic vibrator driving apparatus, an ultrasonic vibrator driving apparatus that applies a sine-waveform or square-waveform drive voltage to a piezoelectric element that defines and functions as an ultrasonic vibrator to cause the ultrasonic vibration of the piezoelectric element to nebulize and spray medicinal liquid.

Incidentally, if the above-described ultrasonic vibrator is of a type in which a piezoelectric element and a horn that transmits the vibration of the piezoelectric element are integrally combined (referred to as a "horn vibrator" as appropriate), as is widely used in order to form a mesh nebulizer for example, the Q value (sharpness of resonance) is extremely high, as can be understood from FIG. 8. For this reason, as shown in FIG. 9, regarding a certain horn vibrator (the unique resonance frequency is denoted as "fr"; the units of fr are kHz), the practical range of frequencies of the driving voltage is limited to the range Δf from (fr-0.8 kHz) to fr. Note that in FIGS. 8 and 9, the horizontal axis indicates the frequency of the drive voltage and the vertical axis indicates the impedance (indicated by the solid line) and the phase (indicated by the broken line) of the horn vibrator.

Furthermore, it is known that there is a manufacturing variation of about ±1.5 kHz in the resonance frequency fr of the horn vibrator. FIG. 10 shows changes in spray amount per unit time when the frequency of a drive voltage composed of a square wave is changed, for three samples, namely samples No. 1 to 3, which have different resonant frequencies due to manufacturing variation. If the frequency of the drive voltage exceeds the resonance frequency fr1=178.85 kHz in Sample No. 1, the resonance frequency fr2=179.15 kHz in Sample No. 2, and the resonance frequency fr3=179.40 kHz in Sample No. 3, each by about 0.03 kHz at most, the spray amount per unit time decreases by about half.

Therefore, for example, if the square-waveform alternating voltage output by a driver IC (Integrated Circuit) is applied as the drive voltage to a horn vibrator as is, the frequency of the drive voltage deviates from the resonance frequency of the horn vibrator and the driving efficiency of the horn vibrator decreases in some cases.

In contrast, if the square-waveform alternating voltage generated by a driver IC (Integrated Circuit) (that is to be the origin of the drive voltage) is applied to a horn vibrator after being converted to a sine-waveform alternating voltage via a conversion circuit that includes inductive reactance elements (L) and capacitive reactance elements (C), reduction of the driving efficiency of the horn vibrator can be suppressed even if the frequency of the drive voltage slightly deviates from the resonance frequency of the horn vibrator, and reduction of the spray amount per unit time can be suppressed. However, if a conversion circuit is simply interposed between the driver IC and the horn vibrator, there is a problem in that a leak current flows to grounding (GND) via the foregoing conversion circuit, and the current consumption increases.

SUMMARY OF THE INVENTION

In view of this, a preferred embodiment of the present invention provides an ultrasonic vibrator driving apparatus that applies a sine-waveform alternating voltage as a drive voltage via a conversion circuit to an ultrasonic vibrator that has a unique resonance frequency, the ultrasonic vibrator driving apparatus being able to reduce or prevent a leak current to grounding.

Also, a preferred embodiment of the present invention provides a mesh nebulizer that includes such an ultrasonic vibrator driving apparatus.

An ultrasonic vibrator driving apparatus according to a preferred embodiment of the present invention is configured to perform driving by applying a drive voltage to an ultrasonic vibrator that includes a piezoelectric element and has a unique resonance frequency, the ultrasonic vibrator driving apparatus including a drive voltage generator to generate a square-waveform alternating voltage that is to be the origin of the drive voltage, with a variable frequency in a frequency range that includes the resonance frequency of the ultrasonic vibrator, a conversion circuit that is interposed in a wiring route from the drive voltage generator to the ultrasonic vibrator to convert the square-waveform alternating voltage generated by the drive voltage generator to a sine-waveform alternating voltage using inductive reactance elements and capacitive reactance elements, the sine-waveform alternating voltage being applied to the ultrasonic vibrator as the drive voltage, a first current detector to detect a first current flowing from the drive voltage generator to the conversion circuit, a second current detector to detect a second current flowing from the conversion circuit to the ultrasonic vibrator, and a frequency controller to perform control of the drive voltage generator to change the frequency of the square-waveform alternating voltage so that the difference between the first current and the second current approaches a minimum.

Here, the "square waveform" includes not only a strict square wave but also any angular waveforms that can substantially be considered square waveforms for use as a drive voltage for the ultrasonic vibrator. Here, the "sine waveform" includes not only a strict sine wave but also smoothly changing waveforms that can substantially be considered sine waves for use as a drive voltage for the ultrasonic vibrator.

With an ultrasonic vibrator driving apparatus according to a preferred embodiment of the present invention, the drive voltage generator generates a square-waveform alternating voltage that is to be the origin of the drive voltage, with a variable frequency in the frequency range that includes the resonance frequency of the ultrasonic vibrator. A conversion circuit interposed in a wiring route from the drive voltage generator toward the ultrasonic vibrator converts the square-waveform alternating voltage generated by the drive voltage generator to a sine-waveform alternating voltage with inductive reactance elements and capacitive reactance elements. The sine-waveform alternating voltage is applied to the ultrasonic vibrator as the drive voltage. Accordingly, even if the frequency of the drive voltage slightly deviates from the resonance frequency of the ultrasonic vibrator, it is possible to suppress a reduction of the driving efficiency. In addition, with this ultrasonic vibrator driving apparatus, the first current detector detects the first current flowing from the drive voltage generator to the conversion circuit, whereas the second current detector detects the second current flowing from the conversion circuit to the ultrasonic vibrator. The frequency controller performs control on the drive voltage generator to change the frequency of the square-waveform alternating voltage so that the difference between the first current and the second current approaches a minimum. When the difference between the first current and the second current is brought close to the minimum by the control, the impedance of the conversion circuit matches the impedance of the ultrasonic vibrator. Accordingly, the difference between the first current and the second current, i.e., the leak current to grounding GND via the conversion circuit, is reduced or prevented. This results in reducing or preventing an increase in current consumption.

With an ultrasonic vibrator driving apparatus of a preferred embodiment of the present invention, the difference between the first current and the second current is the difference between the peak-to-peak value of the first current and the peak-to-peak value of the second current, the difference between the amplitude of the first current and the amplitude of the second current, or the difference between the effective value of the first current and the effective value of the second current.

With an ultrasonic vibrator driving apparatus of this preferred embodiment, the difference is able to be easily obtained regardless of the phases of the first and second currents.

With an ultrasonic vibrator driving apparatus of a preferred embodiment of the present invention, the impedance exhibited by the conversion circuit in the frequency range that includes the resonance frequency of the ultrasonic vibrator is set to substantially match the minimum value of the impedance of the ultrasonic vibrator.

Here, "substantially matching" the minimum value of the impedance of the ultrasonic vibrator includes not only exact matching, but also a range that can be considered to substantially match the minimum from the viewpoint of impedance matching (for example, the range from the minimum value up to about 1.5 times the minimum value).

With an ultrasonic vibrator driving apparatus of this preferred embodiment, the impedance exhibited by the conversion circuit in the frequency range that includes the resonance frequency of the ultrasonic vibrator is set to substantially match the minimum value of the impedance of the ultrasonic vibrator. Here, as described above, when the difference between the first current and the second current is brought close to the minimum due to the control by the conversion circuit, the impedance of the conversion circuit matches the impedance of the ultrasonic vibrator. Accordingly, at that moment, the frequency of the square-waveform alternating voltage approximately matches the resonance frequency of the ultrasonic vibrator (the frequency that provides the minimum value of the impedance of the ultrasonic vibrator). This results in an improved driving efficiency of the ultrasonic vibrator.

With an ultrasonic vibrator driving apparatus of a preferred embodiment of the present invention, the ultrasonic vibrator is a horn vibrator defined by integrally combining the piezoelectric element and a horn to transmit vibration of the piezoelectric element.

With the ultrasonic vibrator driving apparatus of this preferred embodiment, the ultrasonic vibrator is a horn vibrator defined by integrally combining the piezoelectric element and a horn to transmit vibration of the piezoelectric element. Accordingly, even if the frequency of the drive voltage slightly deviates from the resonance frequency of the ultrasonic vibrator, the advantages and benefits of preferred embodiments of the present invention, that is, the ability to suppress a reduction of the driving efficiency, is great.

In another aspect, a mesh nebulizer according to a preferred embodiment of the present invention includes the ultrasonic vibrator driving apparatus of the above-described preferred embodiment of the present invention, the ultrasonic vibrator being a horn vibrator defined by integrally combining the piezoelectric element and a horn to transmit the vibration of the piezoelectric element, and a flat plate-shaped or sheet-shaped mesh portion arranged facing a vibration surface of the horn vibrator, wherein a medicinal liquid supplied between the vibration surface and the mesh portion is nebulized and sprayed through the mesh portion.

In the present specification, the "flat plate-shaped or sheet-shaped mesh portion" means an element that has multiple through holes that penetrate through a flat plate or a sheet and is to nebulize a liquid by passing the liquid through the through holes. Note that "sheet" encompasses a film.

A mesh nebulizer according to a preferred embodiment of the present invention is capable of efficiently nebulizing and spraying the liquid and is capable of suppressing an increase in current consumption.

As is evident from the description above, an ultrasonic vibrator driving apparatus according to a preferred embodiment of the present invention is an ultrasonic vibrator driving apparatus that applies a sine-waveform alternating voltage as a drive voltage via a conversion circuit to an ultrasonic vibrator that has a unique resonance frequency, the ultrasonic vibrator driving apparatus being able to reduce or prevent a leak current to grounding. Also, according to a mesh nebulizer according to a preferred embodiment of the present invention, the liquid is able to be efficiently nebulized and sprayed, and an increase in current consumption is also to be prevented.

The above and other elements, features, steps, characteristics and advantages of the present invention will become more apparent from the following detailed description of the preferred embodiments with reference to the attached drawings.

BRIEF DESCRIPTION OF THE DRAWINGS

FIGS. 6A and 6C are diagrams showing changes in the first current flowing from the foregoing drive voltage generator to the conversion circuit when the frequency of the square-waveform alternating voltage generated by the drive voltage generator is sequentially increased.

FIG. 7A is a diagram showing a change in the first current flowing from the drive voltage generator to the conversion circuit when the frequency of the square-waveform alternating voltage generated by the drive voltage generator is further increased. FIG. 7B corresponds to FIG. 7A, and is a diagram showing a change in the second current flowing from the conversion circuit to the foregoing horn vibrator when the frequency of the square-waveform alternating voltage generated by the drive voltage generator is further increased.

DETAILED DESCRIPTION OF THE PREFERRED EMBODIMENTS

Hereinafter, preferred embodiments of the present invention will be described in detail with reference to the drawings.

Figure 2:
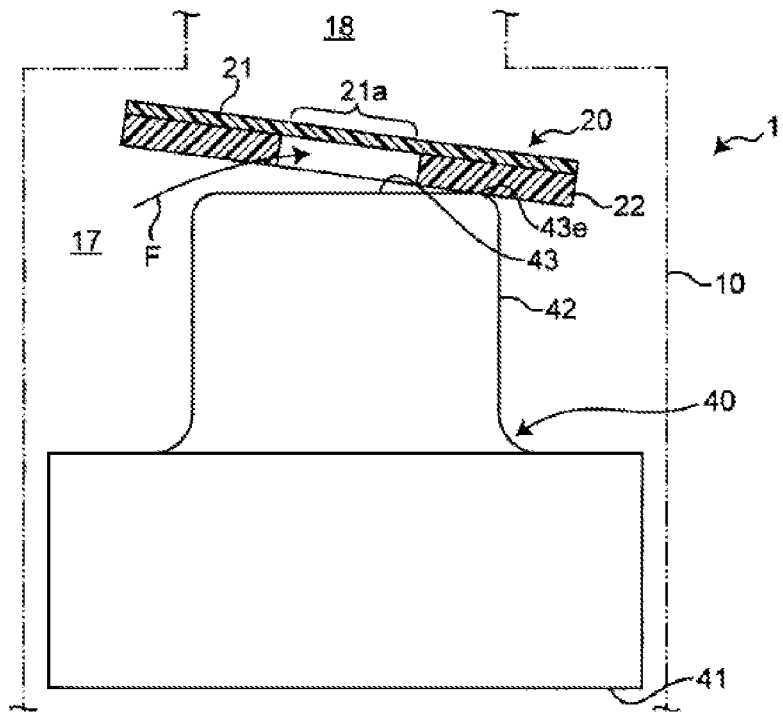
FIG. 2 is a diagram showing a configuration of a nebulization unit of a mesh nebulizer in which an ultrasonic vibrator driving apparatus according to a preferred embodiment of the present invention is mounted.

FIG. 2 shows a configuration of a nebulization unit of a mesh nebulizer (indicated overall by the reference numeral 1) in which an ultrasonic vibrator driving apparatus 1 of a preferred embodiment of the present invention is mounted. The mesh nebulizer 1 includes a main body 10 that has an opening 18 in its upper portion, and a horn vibrator 40 defining and functioning as an ultrasonic vibrator built into the main body 10. A power source switch (not shown) is provided on the outer surface of the main body 10.

Figure 8:
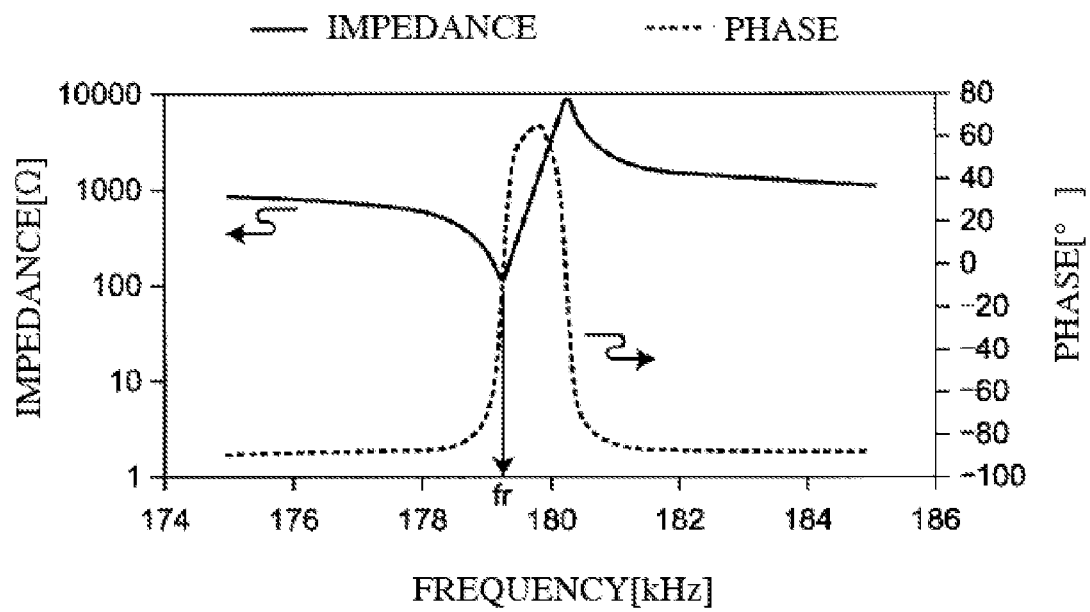
FIG. 8 is a diagram showing changes in impedance (indicated by a solid line) and phase (indicated by a broken line) of the horn vibrator accompanying a change in the frequency of the drive voltage.
Figure 9:
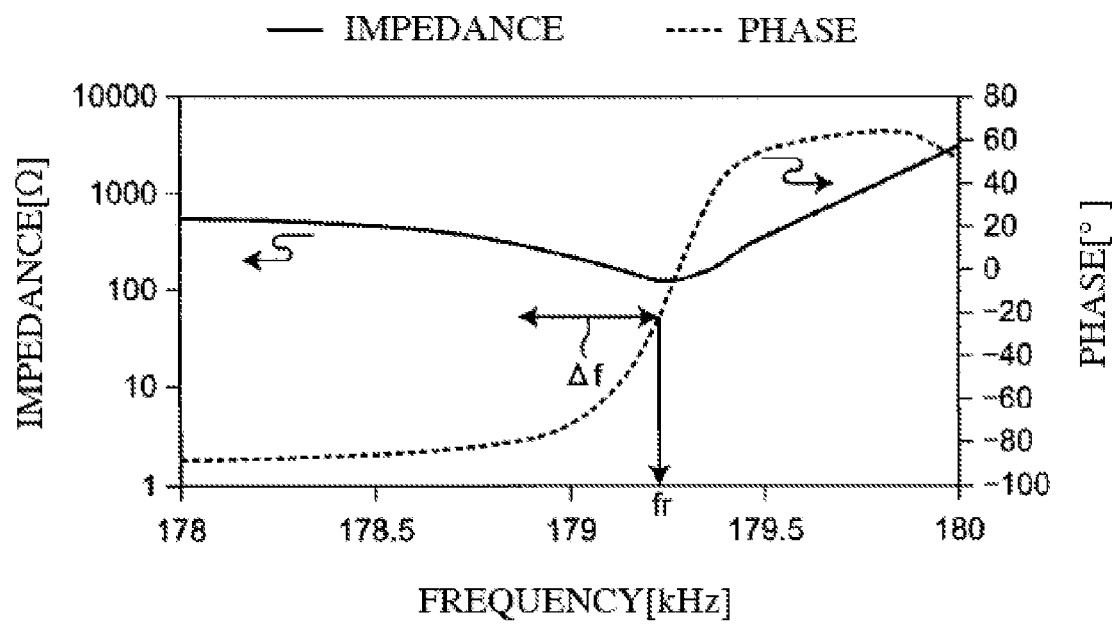
FIG. 9 is a diagram showing a practical range of frequencies of the drive voltage for a certain horn vibrator (resonance frequency is denoted by "fr").
Figure 10:
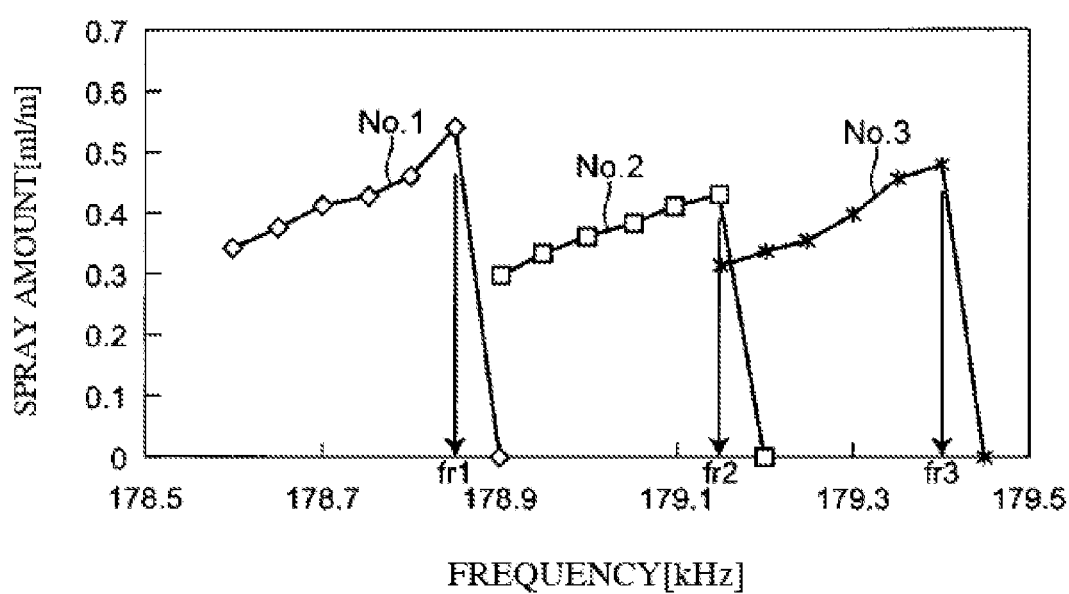
FIG. 10 is a diagram showing changes in spray amount per unit time when the frequency of the drive voltage is changed, for three horn vibrator samples whose resonance frequencies differ due to manufacturing variations.

The horn vibrator 40 is defined by integrally combining a vibration surface 43 horizontally opposing the opening 18 arranged thereabove; a piezoelectric element 41 located at a position separated downward from the vibration surface 43; and a horn 42 that is located between the piezoelectric element 41 and the vibration surface 43 and amplifies and transmits the vibration of the piezoelectric element 41 to the vibration surface 43. The drive voltage for the horn vibrator 40 (more accurately, the piezoelectric element 41) is supplied by a later-described ultrasonic vibrator driving apparatus 60. The horn vibrator 40 has a unique resonance frequency fr, as illustrated in FIGS. 8 and 9.

A replacement member 20 is arranged by being detachably mounted between the opening 18 and the vibration surface 43. The replacement member 20 includes a film 21 defining and functioning as a flat sheet that opposes the vibration surface 43; and an approximately circular ring-shaped bottom plate portion 22 that supports the circumferential edge of the film 21. The film 21 is attached through adhesion or welding to the upper surface of the bottom plate portion 22. An approximately central region of the film 21 is a mesh portion 21a. Many minute through holes (not shown) that penetrate through the film 21 are formed in the mesh portion 21a. The bottom plate portion 22 is in contact at one location with an edge portion 43e of the vibration surface 43 in this example, to perform positioning. The replacement member 20 is supported by the horn vibrator 40 and an element (not shown) of the main body 10, in a state of being slightly inclined with respect to the vibration surface 43. Note that the mesh portion 21a may be defined by forming many minute through holes in a flat plate instead of the film 21.

During operation of the mesh nebulizer 1, the user slightly tilts the main body 10 with respect to the vertical direction. Accordingly, liquid (in this example, medicinal liquid) is supplied from a liquid supply portion 17 in the main body 10 onto the vibration surface 43 of the horn vibrator 40 as indicated by arrow F. In other words, the medicinal liquid is supplied between the vibration surface 43 and the mesh portion 21a. Then, when the user switches on the power source switch, the drive voltage is applied to the piezoelectric element 41 of the horn vibrator 40 and the vibration surface 43 is vibrated via the horn 42. Accordingly, the medicinal liquid is nebulized through the mesh portion 21a (more accurately, through the multiple through holes penetrating through the film 21) and is sprayed through the opening 18.

Figure 1:
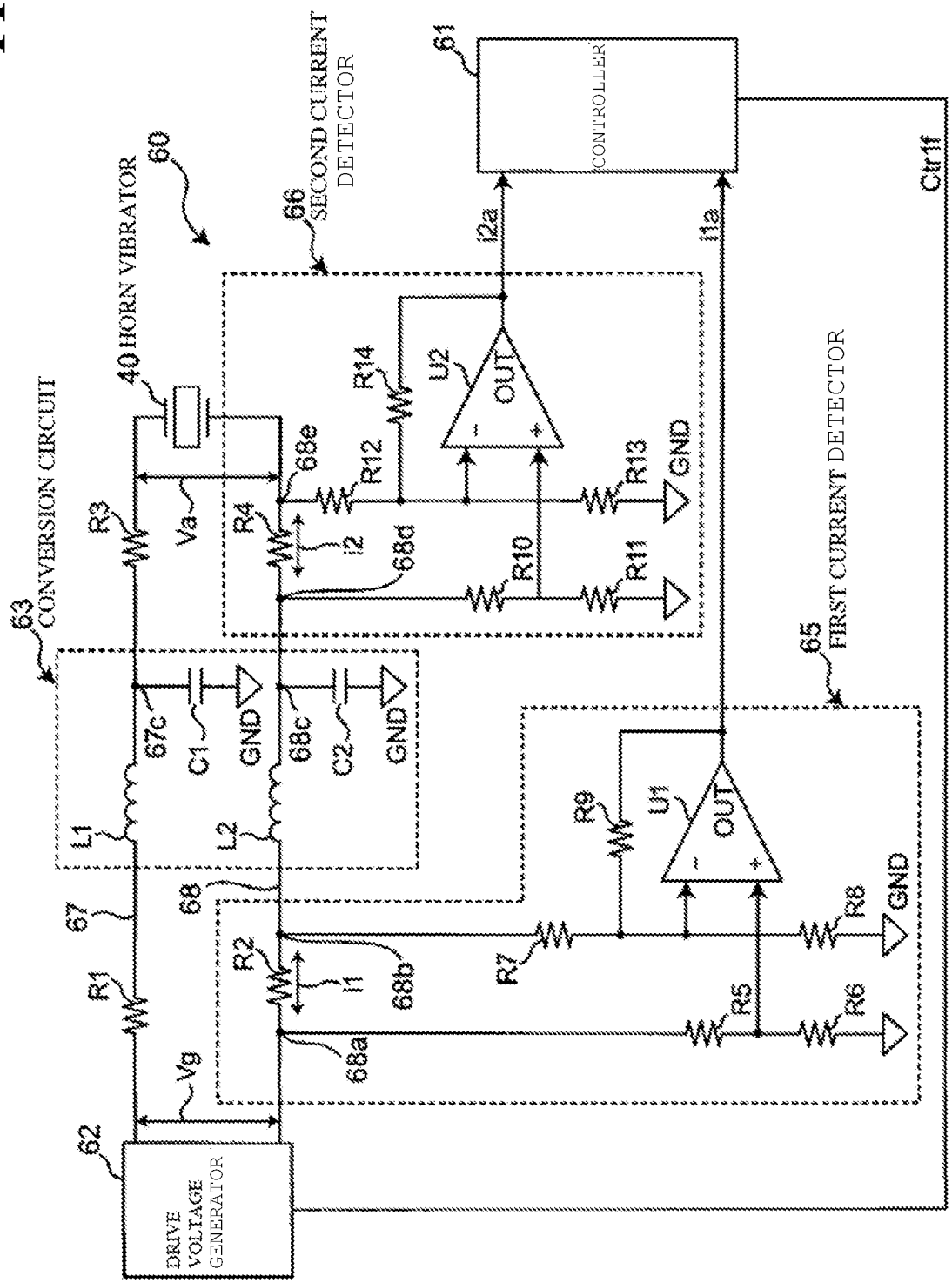
FIG. 1 is a diagram showing a circuit configuration in which a conversion circuit is interposed in a wiring route from a drive voltage generator to a horn vibrator that defines and functions as an ultrasonic vibrator of an ultrasonic vibrator driving apparatus according to a preferred embodiment of the present invention.

FIG. 1 shows a block configuration of the ultrasonic vibrator driving apparatus 60 mounted in the mesh nebulizer 1.

This ultrasonic vibrator driving apparatus 60 includes a drive voltage generator 62, a pair of wires 67 and 68 that defines and functions as a wiring route connected from a drive voltage generator 62 to the horn vibrator 40, and a conversion circuit 63 interposed in the wires 67 and 68. Also, this ultrasonic vibrator driving apparatus 60 includes a first current detector 65, a second current detector 66, and a controller 61 that controls the above-described drive voltage generator 62 based on the outputs of the first current detector 65 and the second current detector 66.

The drive voltage generator 62, for example, includes a commercially available function generator IC (Integrated Circuit) and generates a square-waveform alternating voltage Vg that is to be the origin of the drive voltage, with a variable frequency in a frequency range that includes the resonance frequency fr of the horn vibrator 40. In this example, the drive voltage generator 62 includes a function according to which it is possible to vary the frequency f by about 0.05 kHz at a time, within a range of at least about 175 kHz to about 185 kHz, for example. Also, the ratio between the positive voltage period and the negative voltage period of the alternating voltage Vg is variable, but in this example, it is 1 to 1 (for example, about 50% duty). This drive voltage generator 62 includes an amplifier unit that outputs the alternating voltage Vg, which has sufficient amplitude to drive the horn vibrator 40.

Figure 5A:
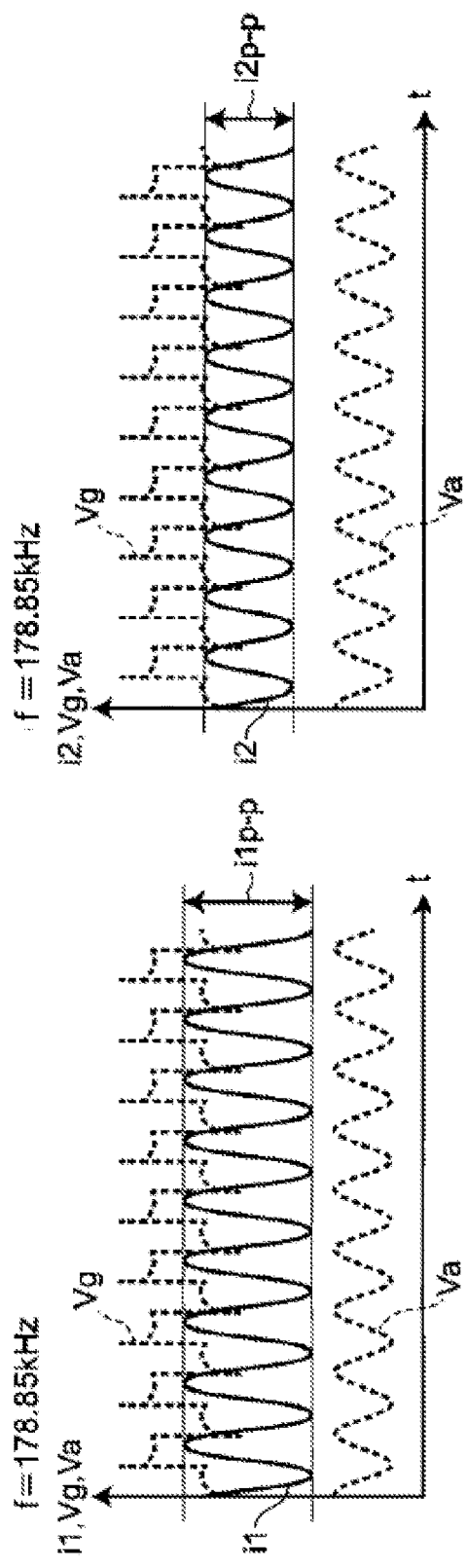
FIGS. 5A and 5C are diagrams showing changes in a first current flowing from the drive voltage generator to the conversion circuit when the frequency of a square-waveform alternating voltage generated by the drive voltage generator is sequentially increased.

The conversion circuit 63 includes a coil L1 that defines and functions as an inductive reactance element interposed in one of the wires or the wire 67, a capacitor C1 that defines and functions as a capacitive reactance element connected between a point 67c of the wire 67 located on the horn vibrator 40 side (which refers to the right side on FIG. 1 and will be simply referred to as the right side hereinafter) of the coil L1 and grounding GND (denoted by the "∇" mark in FIG. 1), a coil L2 that defines and functions as an inductive reactance element interposed in the other wire 68, and a capacitor C2 that defines and functions as a capacitive reactance element connected between a point 68c of the wire 68 located to the right of the coil L2 and grounding GND. As shown in FIG. 5A, this conversion circuit 63 converts the square-waveform alternating voltage Vg generated by the drive voltage generator 62 to a sine-waveform alternating voltage Va. The sine-waveform alternating voltage Va is applied to the horn vibrator 40, which is shown in FIG. 1, as a drive voltage. Accordingly, even if the frequency f of the drive voltage slightly deviates from the resonance frequency fr of the horn vibrator 40, it is possible to suppress a reduction of the driving efficiency.

In this example, the impedance exhibited by the conversion circuit 63 in the frequency range between about 175 kHz and about 185 kHz, which includes the resonance frequency fr of the horn vibrator 40, is set to approximately match the minimum value Zmin of the impedance of the horn vibrator 40 (about 100Ω in this example). Specifically, the settings are L1=L2=about 47 µH and C1=C2=about 4700 pF, for example. In this way, near the frequency f=about 179 kHz, the series impedances L1 and C1 and the series impedances L2 and C2 are each about 136Ω, for example.

The first current detector 65 includes a resistance element R2 for current detection interposed between the drive voltage generator 62 and the coil L2 in the above-described wire 68, and an operational amplifier U1 that amplifies the voltage that drops across the resistance element R2. Voltage-dividing resistance elements R5 and R6 are connected in series between a point 68a located on the drive voltage generator 62 side (which refers to the left side on FIG. 2 and will be simply referred to as the left side hereinafter) of the resistance element R2 and grounding GND in the wire 68. The potential at the junction point between these resistance elements R5 and R6 is input into a noninverting input terminal (+) of the operational amplifier U1. Also, voltage-dividing resistance elements R7 and R8 are connected in series between a point 68b located to the right of the resistance element R2 and grounding GND in the wire 68. The potential at the junction point between these resistance elements R7 and R8 is input into an inverting input terminal (−) of the operational amplifier U1. A feedback resistance element R9 is connected between the output terminal (OUT) and the inverting input terminal (−) of the operational amplifier U1. Due to this configuration, the first current detector 65 detects the first current i1 that flows from the drive voltage generator 62 to the conversion circuit 63 via the resistance element R2. The output i1a of the first current detector 65 is input to the controller 61.

Similarly, the second current detector 66 includes a current-detection resistance element R4 interposed between the coil L2 and the horn vibrator 40 in the above-described wire 68, and an operational amplifier U2 that amplifies the voltage that drops across the resistance element R4. Voltage-dividing resistance elements R10 and R11 are connected in series between a point 68d located to the left of the resistance element R4 and grounding GND in the wire 68. The potential at the junction point between these resistance elements R10 and R11 is input into a noninverting input terminal (+) of the operational amplifier U2. Also, voltage-dividing resistance elements R12 and R13 are connected in series between a point 68e located to the right of the resistance element R4 and grounding GND in the wire 68. The potential at the junction point between these resistance elements R12 and R13 is input into an inverting input terminal (−) of the operational amplifier U2. A feedback resistance element R14 is connected between the output terminal (OUT) and the inverting input terminal (−) of the operational amplifier U1. Due to this configuration, the second current detector 66 detects the second current i2 that flows from the conversion circuit 63 to the horn vibrator 40. The output i2a of the second current detector 66 is input to the controller 61.

In this example, the respective settings are R2=R4=about 100 mΩ, and R5=R6=R7=R8=R9=R10=R11=R12=R13=R14=about 100 kΩ, for example.

Note that in order to strike a balance in the impedances between the wire 67 and the wire 68, a resistance element R1 is interposed between the drive voltage generator 62 and the coil L1 in the wire 67. Also, a resistance element R3 is interposed between the coil L1 and the horn vibrator 40 in the wire 67. In this example, the values of R1 and R3 are equal to R2 and R4, and they are set to R1=R3=about 100 mΩ, for example.

The controller 61 includes a CPU (Central Processing Unit) and functions as a frequency controller to control the operation of the drive voltage generator 62 with a control signal Cnt1f based on the output i1a of the first current detector 65 and the output i2a of the second current detector 66. In addition, the controller 61 controls the overall operation of the mesh nebulizer 1.

Figure 3:
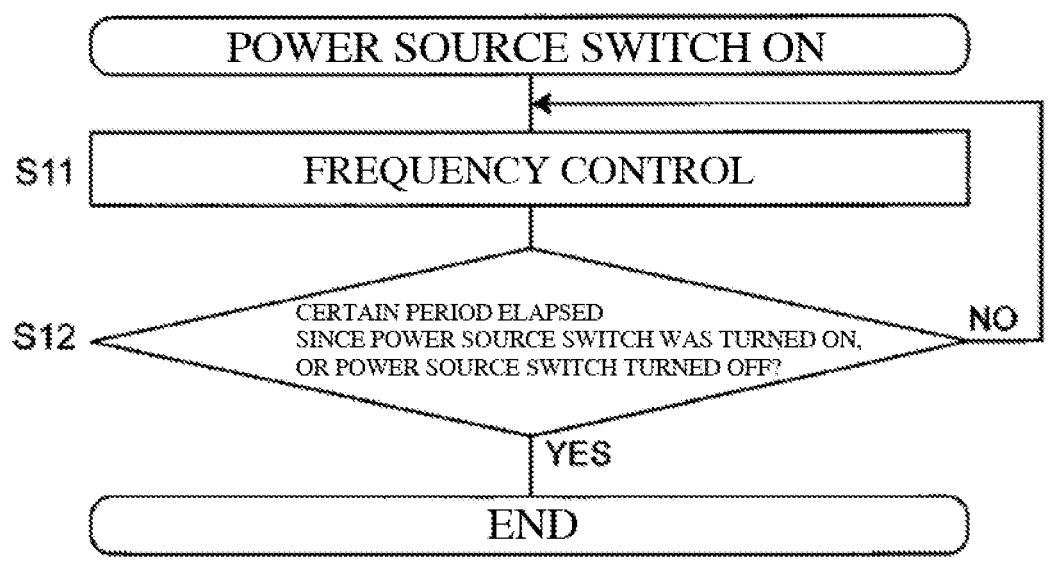
FIG. 3 is a diagram showing an overall flow of control performed by a controller included in an ultrasonic vibrator driving apparatus according to a preferred embodiment of the present invention.

As shown in FIG. 3, when the power source switch of the mesh nebulizer 1 is switched on, the controller 61 functions as a frequency controller to perform frequency control processing as described below (step S11 in FIG. 3). The controller 61 ends the processing when a certain period (e.g., about 10 minutes) has elapsed since the user switched on the power source switch, or when the user switches off the power source switch (step S12 in FIG. 3).

Figure 4:
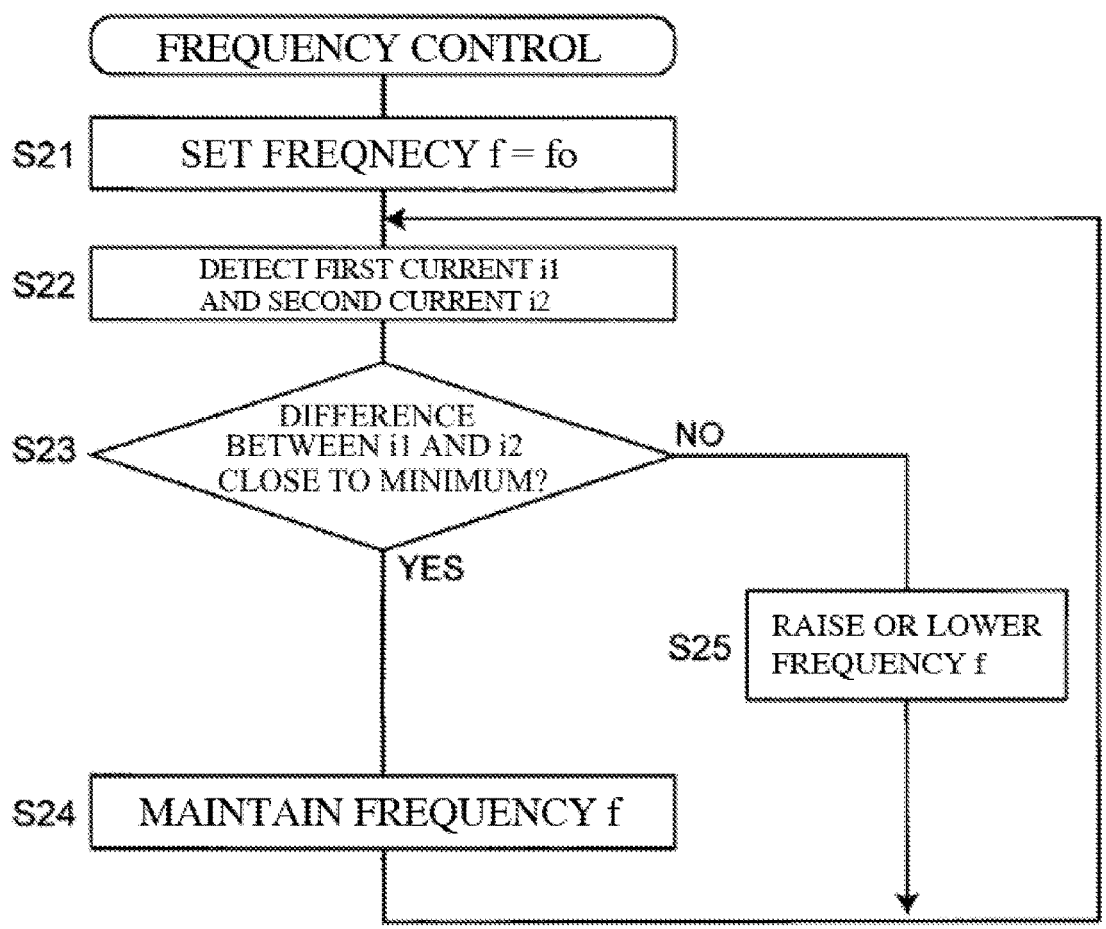
FIG. 4 is a diagram showing the flow of frequency control performed by the controller.

The frequency control processing performed by the controller 61 is performed according to the flow shown in FIG. 4.

That is, as shown in step S21 of FIG. 4, the controller 61 initially sets the frequency f of the square-waveform alternating voltage Vg generated by the drive voltage generator 62 to a predetermined start frequency fo. The start frequency fo may be set, for example, for each horn vibrator 40, or it may be set, for example, to correspond to a representative value (average value) of the resonance frequencies of each lot of the horn vibrator 40 in consideration of the manufacturing variation of the resonance frequencies.

Figure 5B:
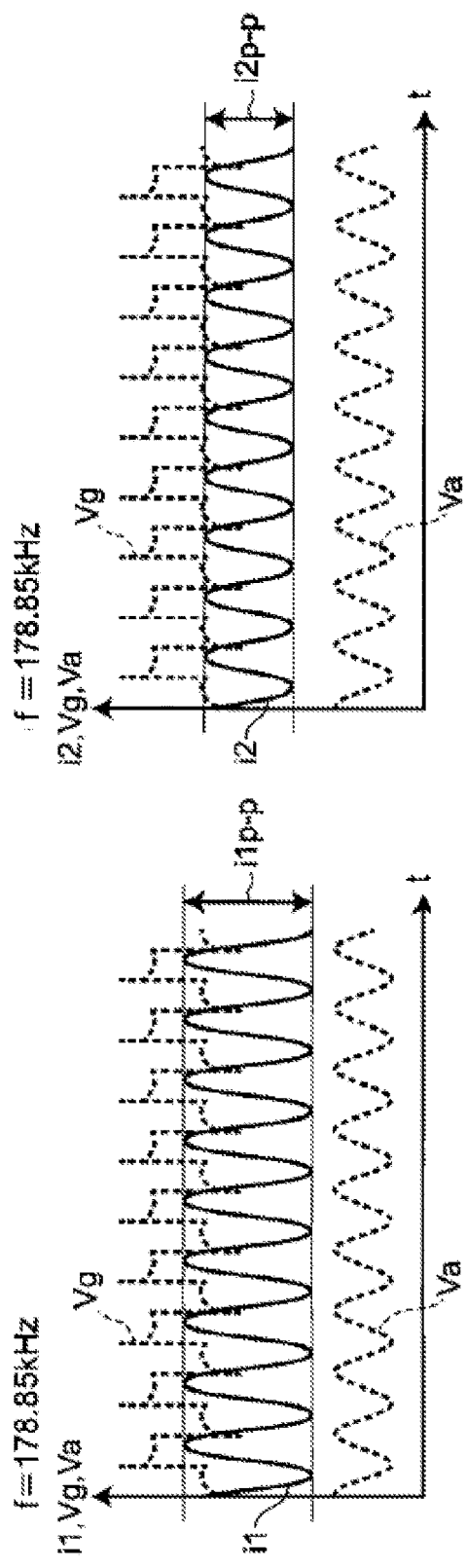
FIGS. 5B and 5D correspond to FIGS. 5A and 5C, and are diagrams showing changes in a second current flowing from the conversion circuit to the horn vibrator when the frequency of the square-waveform alternating voltage generated by the drive voltage generator is sequentially increased.
Figure 5C:
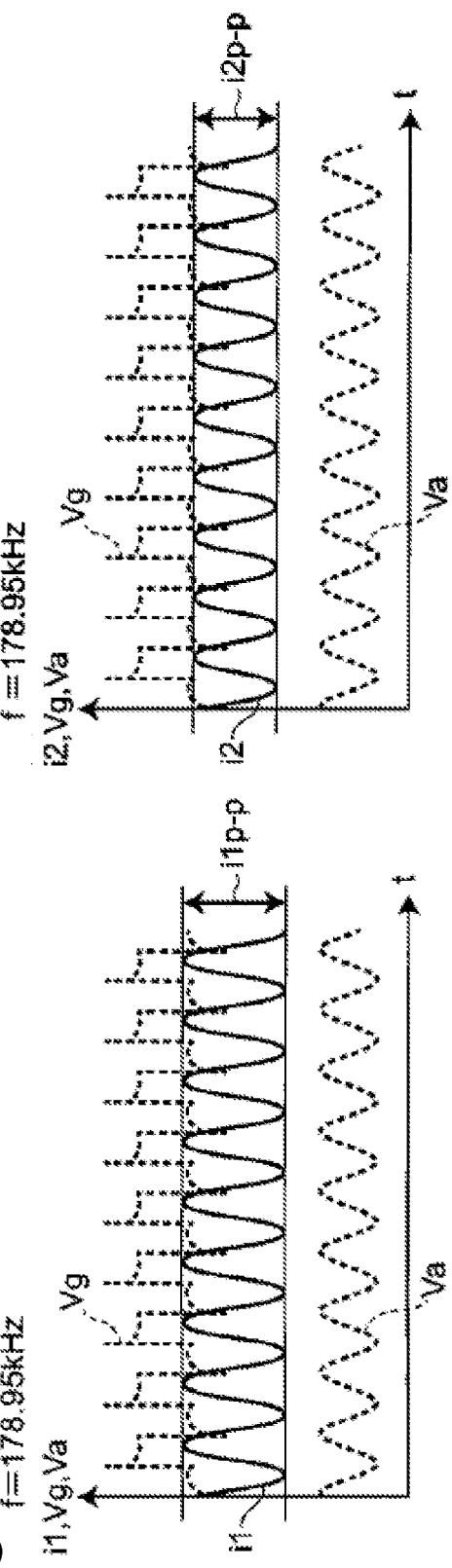
Figure 5D:
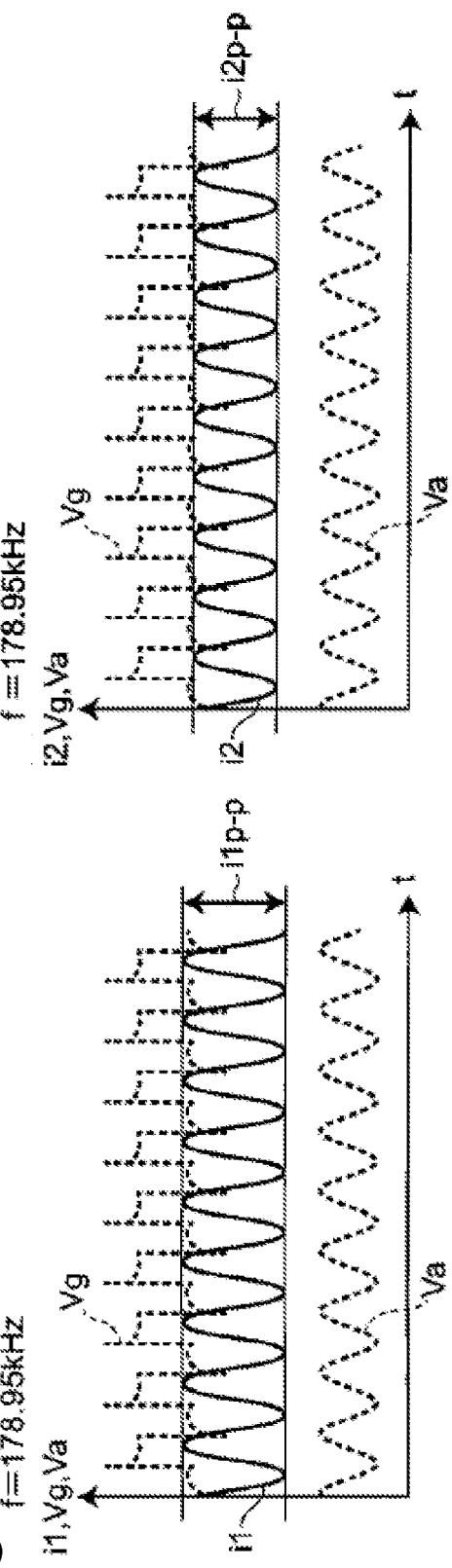
Figure 6A:
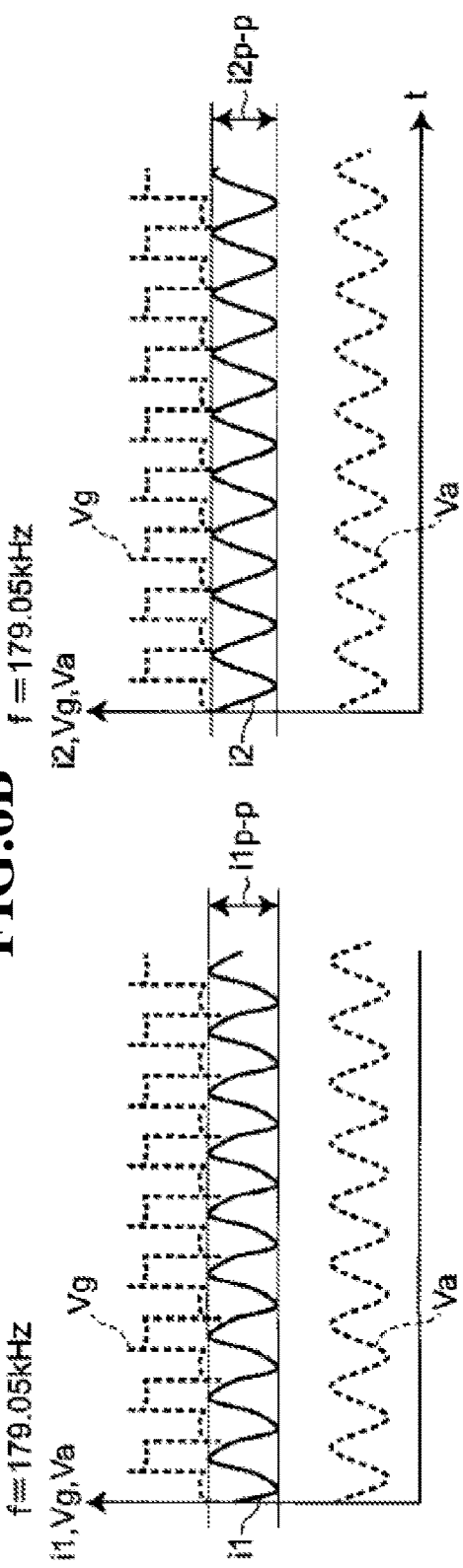
Figure 6B:
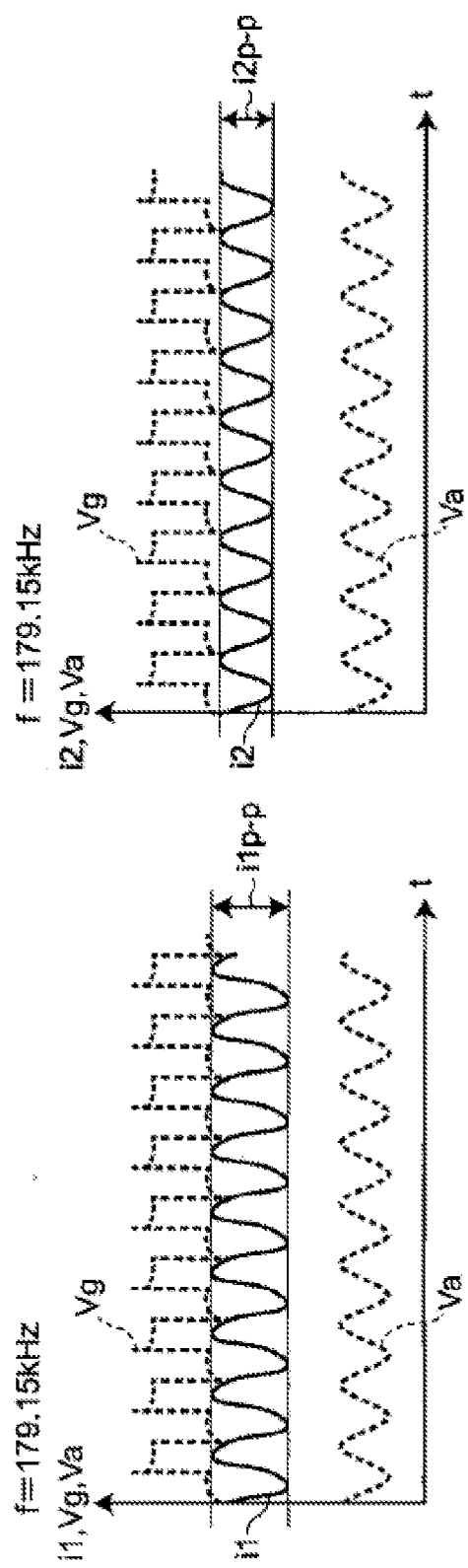
FIGS. 6B and 6D correspond to FIGS. 6A and 6C, and are diagrams showing changes in the second current flowing from the conversion circuit to the horn vibrator when the frequency of the square-waveform alternating voltage generated by the drive voltage generator is sequentially increased.
Figure 6B:
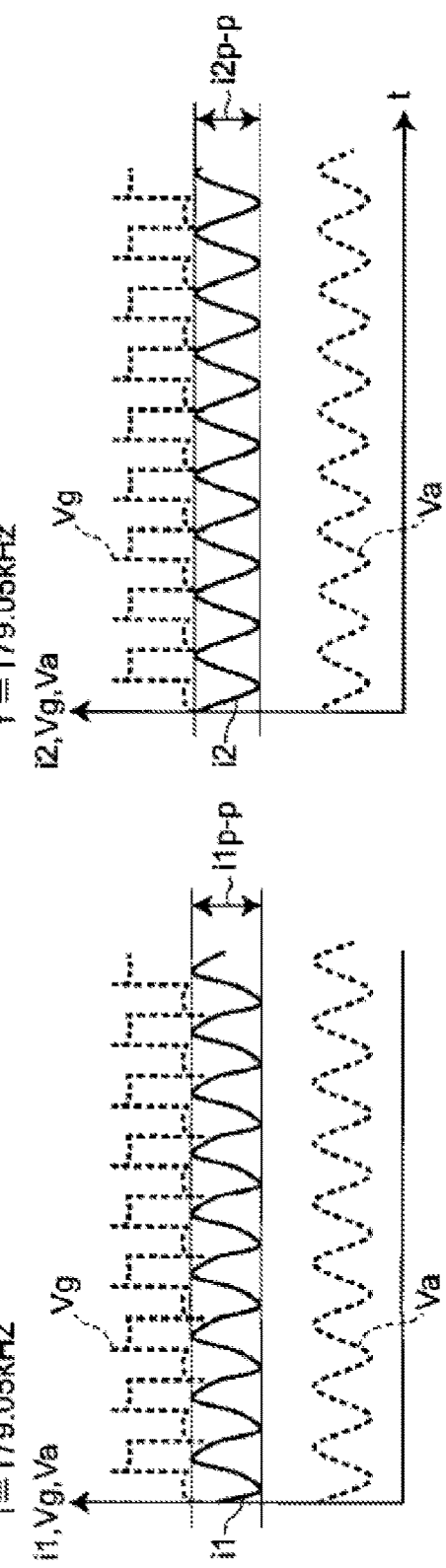
Figure 6D:
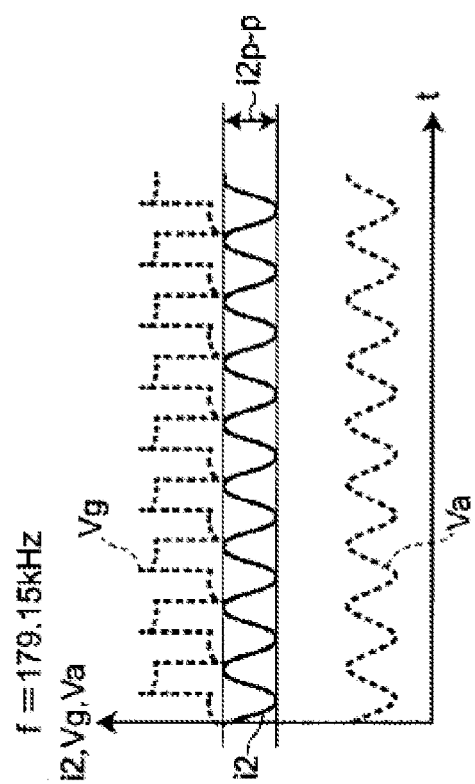

Next, as indicated in step S22 of FIG. 4, the controller 61 detects the first current i1, which flows from the drive voltage generator 62 to the conversion circuit 63, based on the output i1a of the first current detector 65, and the controller 61 detects the second current i2, which flows from the conversion circuit 63 to the transducer 40, based on the output i2a of the second current detector 66. In this example, for instance, the peak-to-peak value i1p-p of the first current i1 is detected as shown in FIG. 5A, and the peak-to-peak value i2p-p of the second current i2 is detected as shown in FIG. 5B.

Next, as indicated in step S23 of FIG. 4, the controller determines whether or not the difference between the first current i1 and the second current i2, in this example, the difference between the peak-to-peak value i1p-p of the first current i1 and the peak-to-peak value i2p-p of the second current i2 (i1p-p-i2p-p) is close to a minimum. Here, it is possible to determine whether or not it is close to the minimum according to whether or not the difference (i1p-p-i2p-p) is no more than a predetermined threshold value.

Here, if the difference (i1p-p-i2p-p) is close to the minimum (YES in step S23 of FIG. 4), the controller 61 performs control to cause the drive voltage generator 62 to maintain the frequency f of the square-waveform alternating voltage Vg. Then, the processing of steps S22-S24 is repeated.

On the other hand, if the difference (i1p-p-i2p-p) is not close to the minimum (NO in step S23 of FIG. 4), the controller 61 performs control to cause the drive voltage generator 62 to raise or lower the frequency f of the square-waveform alternating voltage Vg so that the difference (i1p-p-i2p-p) becomes close to the minimum (step S25 of FIG. 4). Then, the controller 61 repeats the processing of steps S22-S23 and S25 until the difference (i1p-p-i2p-p) becomes close to the minimum.

In this way, when the difference between i1p-p and i2p-p (i1p-p-i2p-p) is brought close to the minimum by the above-described control, the impedance of the conversion circuit 63 matches the impedance of the horn vibrator 40. Accordingly, the difference between the first current i1 and the second current i2, i.e., the leak current to the grounding GND via the conversion circuit 63, is reduced or prevented. This results in reducing or preventing the increase in current consumption.

For the purpose of verification, FIGS. 5A and 5C, FIGS. 6A and 6C, and FIG. 7A show, with respect to a horn vibrator 40, the changes in the first current i1 flowing from the drive voltage generator 62 to the conversion circuit 63 when the frequency f of the square-waveform alternating voltage Vg generated by the drive voltage generator 62 is sequentially increased from f=about 178.85 kHz by about 0.1 kHz at a time. These figures show the peak-to-peak value i1p-p of the first current i1. Also, FIGS. 5B and 5B, FIGS. 6B and 6D, and FIG. 7B correspond to FIGS. 5A and 5C, FIGS. 6A and 6C, and FIG. 7A, respectively, and show the changes in the second current i2 flowing from the conversion circuit 63 to the horn vibrator 40 when the frequency f of the square-waveform alternating voltage Vg generated by the drive voltage generator 62 is sequentially increased from f=about 178.85 kHz by about 0.1 kHz at a time. These figures show the peak-to-peak value i2p-p of the second current i2. Furthermore, in these figures, for ease of understanding, the square-waveform alternating voltage Vg generated by the drive voltage generator 62 and the sine-waveform alternating voltage Va after being converted by the conversion circuit 63 are shown with the zero levels shifted.

The peak-to-peak value i1p-p of the first current i1 and the peak-to-peak value i2p-p of the second current i2 in these figures were as indicated in the second and third columns from the left of Table 1 below. Also, the calculated differences between i1p-p and i2p-p (i1p-p-i2p-p) were as indicated in the rightmost column of Table 1. Note that the reading of i1p-p and i2p-p and the calculation of the difference (i1p-p-i2p-p) were performed in a common unit (any unit used by the CPU to perform digital processing). In the results, the difference (i1p-p-i2p-p) changed from approximately 109 to 80 to 24 to 56 and to 68 as the frequency f of the square-waveform alternating voltage Vg was sequentially increased from f=about 178.85 kHz by about 0.1 kHz at a time. That is to say, at the frequency of f=about 179.05 kHz, the difference (i1p-p-i2p-p) became approximately 24, which is the minimum or is close thereto.

TABLE 1

| Frequency f | i1p-p | i2p-p | Difference (i1p-p − i2p-p) |
|---|---|---|---|
| 178.85 kHz | 302 | 193 | 109 |
| 178.95 kHz | 257 | 177 | 80 |
| 179.05 kHz | 181 | 157 | 24 (Close to the minimum) |
| 179.15 kHz | 193 | 137 | 56 |
| 179.25 kHz | 185 | 117 | 68 |

Accordingly, in the case of this horn vibrator 40, due to the above-described frequency control by the controller 61, the drive voltage generator 62 controls (maintains) the frequency f of the square-waveform alternating voltage Vg to f=about 179.05 kHz. This results in reducing or preventing the leak current to the grounding GND via the conversion circuit 63 to reduce or prevent the increase in current consumption.

Also, as described above, the impedance exhibited by the conversion circuit 63 in the frequency range between about 175 kHz and about 185 kHz, which includes the resonance frequency fr of the horn vibrator 40, is set to approximately match the minimum value Zmin of the impedance of the horn vibrator 40 (about 100Ω in this example). Here, when the difference between i1p-p and i2p-p (i1p-p-i2p-p) is brought close to the minimum by the above-described frequency control, the impedance of the conversion circuit 63 matches the impedance of the horn vibrator 40. Accordingly, at that moment, the frequency f of the square-waveform alternating voltage Vg approximately matches the resonance frequency fr of the horn vibrator 40 (the frequency that provides the minimum value of the impedance of the horn vibrator 40≈100Ω). This results in an improved driving efficiency of the horn vibrator 40.

Accordingly, this mesh nebulizer 1 is capable of efficiently nebulizing and spraying medicinal liquid and also capable of reducing or preventing the increase in current consumption.

Note that, in the foregoing example, the difference between the first current i1 and the second current i2 is the difference between the peak-to-peak value i1p-p of the first current i1 and the peak-to-peak value i2p-p of the second current i2 (i1p-p-i2p-p). However, there is no limitation to this. The difference between the first current i1 and the second current i2 may be the difference between the amplitude of the first current i1 and the amplitude of the second current i2, or it may also be the difference between the effective value of the first current i1 and the effective value of the second current i2. In either case, the above-described "difference" is able to be easily obtained regardless of the phases of the first and second currents.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An ultrasonic vibrator driving apparatus configured to perform driving by applying a drive voltage to an ultrasonic vibrator that includes a piezoelectric element and has a resonance frequency, the ultrasonic vibrator driving apparatus comprising:

a drive voltage generator to generate a square-waveform alternating voltage that is to be an origin of the drive voltage, with a variable frequency in a frequency range that includes the resonance frequency of the ultrasonic vibrator;

a conversion circuit that is interposed in a wiring route from the drive voltage generator to the ultrasonic vibrator to convert the square-waveform alternating voltage generated by the drive voltage generator to a sine-waveform alternating voltage using inductive reactance elements and capacitive reactance elements, the sine-waveform alternating voltage being applied to the ultrasonic vibrator as the drive voltage;

a first current detector to detect a first current flowing from the drive voltage generator to the conversion circuit;

a second current detector to detect a second current flowing from the conversion circuit to the ultrasonic vibrator; and a frequency controller to perform control on the drive voltage generator to change the frequency of the square-waveform alternating voltage so that a difference between the first current and the second current approaches a minimum.

2. The ultrasonic vibrator driving apparatus according to claim 1, wherein the difference between the first current and the second current is one of a difference between a peak-to-peak value of the first current and a peak-to-peak value of the second current, a difference between an amplitude of the first current and an amplitude of the second current, or a difference between an effective value of the first current and an effective value of the second current.

3. The ultrasonic vibrator driving apparatus according to claim 1, wherein an impedance exhibited by the conversion circuit in a frequency range that includes the resonance frequency of the ultrasonic vibrator substantially matches a minimum value of an impedance of the ultrasonic vibrator.

4. The ultrasonic vibrator driving apparatus according to claim 1, wherein the ultrasonic vibrator is a horn vibrator defined by an integral structure including the piezoelectric element and a horn to transmit vibration of the piezoelectric element.

5. A mesh nebulizer comprising:

the ultrasonic vibrator driving apparatus according to claim 4; and a flat plate-shaped or sheet-shaped mesh portion facing a vibration surface of the horn vibrator; wherein a medicinal liquid supplied between the vibration surface and the mesh portion is nebulized and sprayed through the mesh portion.

* * * * *